United States Patent
Allen et al.

(10) Patent No.: US 6,559,363 B1
(45) Date of Patent: May 6, 2003

(54) COTTON PLANTS WITH IMPROVED COTTON FIBER CHARACTERISTICS AND METHOD FOR PRODUCING COTTON FIBERS FROM THESE COTTON PLANTS

(75) Inventors: Randy Dale Allen, Lubbock, TX (US); Yoshihisa Kasukabe, Ohtsu (JP); Izumi Ihara, Ohtsu (JP); Yoshihiko Maekawa, Ohtsu (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 09/834,659

(22) Filed: Apr. 16, 2001

Related U.S. Application Data

(62) Division of application No. 09/347,669, filed on Jul. 5, 1999, now abandoned.

(51) Int. Cl.[7] .............................. A01H 5/00; A01H 1/00; C07H 21/04; C12N 15/82
(52) U.S. Cl. ...................... 800/314; 800/290; 800/278; 536/23.6; 435/468
(58) Field of Search ................................. 800/287, 290, 800/278, 314; 435/468, 419; 536/23.6

(56) References Cited

U.S. PATENT DOCUMENTS

| | | | |
|---|---|---|---|
| 5,244,802 A | 9/1993 | Rangan | 435/240 |
| 5,495,070 A | 2/1996 | John | 800/205 |
| 5,521,078 A | 5/1996 | John | 435/172.3 |
| 5,597,718 A | 1/1997 | John et al. | 435/172.3 |
| 5,880,110 A | 3/1999 | Kasukabe et al. | 504/291 |
| 5,932,713 A | 8/1999 | Kasukabe et al. | 536/23.6 |
| 6,166,293 A | 12/2000 | Kasukabe et al. | 800/298 |

FOREIGN PATENT DOCUMENTS

| WO | WO 95/08914 | 4/1995 |
|---|---|---|
| WO | WO 96/26639 | 9/1996 |

OTHER PUBLICATIONS

Burgess et al., Possible Dissociation of the Heparin–binding and Mitogenic Activities of Heparin–binding ( Acidic Fibroblast) . . . , 1990, The Journal of Cell Biology, vol. 111, pp. 2129–2138.*

Bowie et al., Deciphering the Message in Protein Sequences: Tolerance to Amino Acid Substitutions, Mar. 1990, Science, vol. 247, pp. 1306–1310.*

Inhibtion of Nopaline Synthase and Peroxidase Expression in Tobacco Expressing Antisense RNA, 1990, Plant Gene Transfer, pp. 135–141.*

Lonneborg et al., Oct. 2001, Plant Cell Reports, vol. 20, No. 7, pp. 596–603.*

*Changes in Indoleacetic Acid Oxidase and Peroxidase Activities During Cotton Fibre Development*, Z. Pflanzenphysiol. Bd. 106, 1982, N. Rama Rao et al., pp. 157–65.

*Role of Peroxidase and Esterase Activities During Cotton Fiber Development*, J. Plant Growth Regulation (1986), Vrinda S. Thaker et al., 5:17–27.

*Structure of the horseradish peroxidase isozyme C genes*, Eur. J. Biochem. 173, (1988), Kazuhito Fujiyama et al., pp. 681–7.

*Isolation and characterization of a pea catalase cDNA*, Plant Molecular Biology, vol. 17, 1991, Sibel H. Isin et al., pp. 1263–5.

Endo–xyloglucan Transferase, a Novel Class of Glycosyltransferase That Catalyzes Transfer of a Segment of Xyloglucan Molecule to Another Xyloglucan Molecule, Journal of Biological Chemistry, vol. 267, No. 29, 1992, Kazuhiko Nishitani et al., pp. 21058–64.

*Molecular Cloning and cDNA Sequencing of Endoxyloglucan Transferase, a Novel Class of Clycosyltransferase That Mediates Molecular Grafting between Matrix Polysaccharides in Plant Cell Walls*, Journal of Biological Chemistry, vol. 268, , No. 34, 1993, Kazuhide Okazawa et al., pp. 25364–68.

*Characterization of two tomato fruit–expressed cDNAs encoding xyloglucan endo–transglycosylase*, Plant Molecular Biology, vol. 28, 1995, D.A. Arrowsmith et al., pp. 391–403.

*Structural characterization of genes corresponding to cotton fiber mRNA, E6: reduced E6 protein in transgenic plants by antisense gene*, Plant Molecular Biology, vol. 30, 1996, Maliyakal E. John, pp: 297–306.

*Changes in Levels of mRNAs for Cell Wall–Related Enzymes in Growing Cotton Fiber Cells*, Plant Cell Physiol., vol. 38, No. 3, 1997, Yoshinori Shimizu et al., pp: 375–8.

*Gene expression in cotton (Gossypium hirsutum L.) fiber: Cloning of the mRNAs*, Proc. Natl. Acad. Sci., USA, vol. 89, Jul. 1992, Maliyakal E. John et al., pp: 5769–73.

* cited by examiner

Primary Examiner—Elizabeth F. McElwain
Assistant Examiner—Stuart J Baum
(74) Attorney, Agent, or Firm—Morrison & Foerster LLP

(57) ABSTRACT

Cotton plants of the genus Gossypium with improved cotton fiber characteristics are disclosed. The cotton plant has an expression cassette containing a gene coding for an enzyme selected from the group consisting of endoxyloglucan transferase, catalase and peroxidase so that the gene is expressed in cotton fiber cells to improve the cotton fiber characteristics. Also disclosed is a method for producing cotton fibers with improved fiber characteristics from these cotton plants.

12 Claims, 3 Drawing Sheets

SEQUENCE LISTING

<160> NUMBER OF SEQ ID NOS: 3

<210> SEQ ID NO 1
<211> LENGTH: 1035
<212> TYPE: DNA
<213> ORGANISM: Gossypium barbadense
<220> FEATURE:
<221> NAME/KEY: CDS
<222> LOCATION: (32)...(901)
<300> PUBLICATION INFORMATION:
<310> PATENT DOCUMENT NUMBER: US, A, 5880110
<311> PATENT FILING DATE: 1995-02-21
<312> PUBLICATION DATE: 1999-03-09
<313> RELEVANT RESIDUES: 1, (1)...(1035)

<400> SEQUENCE: 1

```
caataattct ctctgtttct ctggtttaaa catgggtatg ggtttaagga atggatttct      60
tttgatttta tcttgtgttg ttacactttc cctctcagtt ttgggcgac ctgccacttt     120
ccttgaagat tttagaatca cttggtctga ttctcatatt aggcaaatcg atggagggag    180
agccatccaa cttgttctcg accaaaattc aggctgtgga tttgcttcta aaaggcagta    240
tttgttcgga cgtgtcagca tgaaaatcaa gctcatcccc ggcgactccg ccggaacagt    300
caccgccttt tatatgaatt ctgttacaga tgctgtgcga gatgagctag acttcgagtt    360
cttgggaaac cgtaccgggc agccatatac ggttcaaacc aatatctatg cccatggaaa    420
gggtgacagg gaacaaaggg ttaacctttg gttcgatcct gctgcagatt tccatactta    480
ctcaatcatg tggaaccatc atcagattgt gttctatatt gatgaagtgc caattagggt    540
ttataagaac aatgaagcta gaaatatccc atacccaaaa ctccagccaa tgggagttta    600
ttcaacgctg tgggaggctg atgattgggc aacaagggga ggtttagaga aaattgattg    660
gaccaaagct ccgttcttag cttattacaa ggacttcgac attgaaggat gtccggttcc    720
agggccagta aactgtgcca caaacagtag gaactggtgg gagggcactg cttatcaagc    780
ccttaatgcc atggaagcta aaagatatag ttgggttcgt atgaaccacg tgatatacga    840
ttactgcacc gacaagtccc gttacccggt taccccaccg gagtgcatgt ccatcatctg    900
aaaatccaaa cccaagtgaa gtttcgtgtc ctattttacg tacatatgta cctcccttta    960
tacaaataat agagccatgc aaaaattggg ttttaaaaaa aaaaaaaaaa aaaaaaaaaa   1020
aaaaaaaaaa aaaaa                                                   1035
```

<210> SEQ ID NO 2
<211> LENGTH: 1738
<212> TYPE: DNA
<213> ORGANISM: Pisum sativum
<220> FEATURE:
<221> NAME/KEY: CDS
<222> LOCATION: (57)...(1541)
<300> PUBLICATION INFORMATION:
<301> AUTHORS: Sibel H. Isin and Randy D. Allen
<302> TITLE: Isolation and characterization of a pea catalase cDNA
<303> JOURNAL: Plant Molecular Biology
<304> VOLUME: 17
<306> PAGES: 1263-1265
<307> DATE: 1991

<400> SEQUENCE: 2

```
attttctcta atccctatct tctgctccac caccaccgtc tatcgcttcc atttccatgg      60
atccttacaa gcatcgtcct tctagcgctt tcaattctcc tttctggact acgaactccg    120
gtgctcctgt ttggaataat aactcttccc taaccgttgg atctagaggt ccaattctat    180
```

```
tggaagatta tcatcttgtg gaaaagcttg cccaatttga tagggaaagg atcccagaac      240
gtgttgtcca tgctagggga gcaagtgcaa agggtttctt tgaagtcaca catgatattt      300
cgcacctgac atgtgcagat ttccttcgag ccctgtgt   tcagacacct gtcattgtgc      360
gtttctcaac tgtcattcat gaacgtggca gccctgaaac cttgagggat ccccgaggtt      420
ttgctgtgaa attttacacc agagaggta  actatgacct tgttggaaac aactttcccg      480
tcttcttcgt tcatgacggt atgaattttc cagatatggt ccatgctctt aaacccaatc      540
cccagaccca catccaggag aattggagaa ttcttgattt cttctacaac tttccagaaa      600
gccttcacat gttctccttc ctatttgatg atgtgggtgt cccacaagat tataggcata      660
tggatggttt tggagttaac acatacaccc tgatcaacaa ggctgaaaaa tcggtgtatg      720
tcaaatttca ctggaagccc acctgtggtg tgaagtgtct attggaggaa gaggccattc      780
aggtgggagg atccaaccac agccatgcta ctaaagacct tatgactca  attgctgctg      840
gtaactatcc tgagtggaaa ctttacattc aaacaataga tcctgctcat gaagacagat      900
ttgagtttga cccacttgat gtaactaaga cttggcccga ggacatcata ccccttcagc      960
ccgtaggtcg catggtcttg aacaagaaca tagataattt ctttgctgag aatgaacagc     1020
ttgcattttg tcctgccatt atgctgcctg gtatatatta ctcagatgac aagatgcttc     1080
aaactagggt tttctcttat gctgattcac agaggcacag acttggaccg aactacctgc     1140
aacttcctgt taatgctccc aagtggtctc accacaacaa tcaccatgag ggtttcatga     1200
atgccattca cagggatgag gaggtcaatt acttcccttc aaggcatgat actgttcgtc     1260
atgcagaaag ggtcccccat cctactactc atttatctgc aaggcgtgaa aagtgcaata     1320
ttccgaaaca gaatcacttc aagcaggctg gagaaagata ccgaacttgg gcacctgaca     1380
ggcaggaaag atttctccgc agtgggtag  aagctttatc cgacaccgat ccacgcatca     1440
cccatgaaat ccgcagcatt tgggtatcat actggtctca ggctgatcgt tctcttgggc     1500
agaagttagc atctcatctg aacatgaggc ctagcattta actttgttgc caaatattga     1560
atcatcgcaa gatttgcaga tgtgcaaaat gtatgataaa ggatgtttgt ttggattact     1620
tgaaaagact tttatttttt gttataattt tatatcgtga atgtatacca taaattctat     1680
gtatgcaact cgttgagatg ttacaataaa tccgtaggca tgtgttagtg ttaaaaaa      1738
```

<210> SEQ ID NO 3
<211> LENGTH: 1062
<212> TYPE: DNA
<213> ORGANISM: Armoracia rusticana
<220> FEATURE:
<221> NAME/KEY: CDS
<222> LOCATION: (1)...(1062)
<300> PUBLICATION INFORMATION:
<301> AUTHORS: Kazuhito FUJIYAMA et al.
<302> TITLE: Structure of the horseradish peroxidase isozyme C genes
<303> JOURNAL: European Journal of Biochemistry
<304> VOLUME: 173
<306> PAGES: 681-687
<307> DATE: 1988

<400> SEQUENCE: 3

```
atgcatttct cttcttcttc tactttgttc acttgtataa ccttaatccc attggtatgt       60
cttattcttc atgcttcttt gtctgatgct caacttaccc ctaccttcat cgacaattca      120
tgtcctaatg tctctaacat cgtacgggat actattgtca atgagctaag atcagaccct      180
cgtattgccg cgagcatcct tcgtcttcac ttccacgact gctttgttaa tggttgtgac      240
```

-continued

```
gcatcgatct tgttagacaa cacaacatca tttcgaacag agaaagatgc gtttggaaac    300
gcaaactcgg caagaggatt tccagtgatt gatagaatga aagccgcggt ggagagtgca    360
tgcccaagaa ccgtttcatg cgcagatttg ctcaccattg cagctcaaca atctgtcact    420
ttggcgggag gtccttcttg gagagttcct ttgggcagaa gagatagctt acaagcattt    480
ctggatcttg ctaatgcaaa tcttccagct ccattcttca cacttccaca acttaaagac    540
agctttagaa atgttggcct caaccgttct tctgatctcg ttgcactgtc cggggccac     600 acatttggta aaaatcagtg tcggtttatt atggacagat tatacaactt cagcaacacc    660
ggtttacccg atcctactct caacactact tatctccaaa ctcttcgtgg actatgtccc    720
ctcaatggta atctaagcgc tttggtggat tttgatctac gtacgccaac gatttttgac    780
aacaaatact atgtgaatct cgaagagcaa aaaggactta tccaaagcga ccaagagttg    840
ttctctagcc ccaatgccac tgacacaatc cctttggtga gatcatttgc taatagcaca    900
caaacattct tcaatgcgtt tgtggaggcg atggatagga tgggaaacat tacacctctt    960
acaggaactc aaggacagat caggttgaat tgtagggtgg tgaactccaa ctctctactc   1020
catgatatgg tggaggtcgt tgactttgtt agctctatgt ga                      1062
```

COTTON PLANTS WITH IMPROVED COTTON FIBER CHARACTERISTICS AND METHOD FOR PRODUCING COTTON FIBERS FROM THESE COTTON PLANTS

This application claims priority under 35 U.S.C. §120 to and is a divisional application of U.S. application Ser. No. 09/347,669 filed Jul. 5, 1999 now abandoned.

FIELD OF THE INVENTION

The present invention relates to cotton plants that produce cotton fibers with improved fiber characteristics such as increased fiber length, increased fiber fineness and higher fiber strength, and it also relates to a method for producing cotton fibers from these cotton plants.

BACKGROUND OF THE INVENTION

Cotton fibers are usually produced by cultivating cotton plants of the genus Gossypium and collecting the cotton fibers from the capsules (cotton bolls) formed on the cotton plants. There are many varieties of cotton plant, from which cotton fibers with different fiber characteristics can be obtained and used for various applications depending on their fiber characteristics. Cotton fibers are characterized by various properties among which fiber length, fiber fineness and fiber strength are particularly important. Many efforts have been made so far to improve the characteristics of cotton fibers. Attempted improvements have been mainly focused on fiber length and fiber fineness. In particular, there has been a great demand for longer and finer cotton fibers. The variety of cotton plant known as Sea Island is famous for desired fiber characteristics; however, this variety of cotton plant exhibits a poor yield of cotton fibers and therefore the price of Sea Island cotton fibers is very high. If highly yielding cotton plants with cotton fiber characteristics equal to or better than those of Sea Island cotton can be produced, it will be a great contribution to industry.

The methods for improving the characteristics or yield of cotton fibers can be roughly classified into the following three categories:

1. Variety Improvement by Cross Breeding

This method has been utilized most widely so far. At present, almost all the cultivated varieties of cotton plant are bred by this method. However, much time is needed for this method and the degree of variability is limited, so that one cannot expect remarkable improvements in the cotton fiber characteristics or in the yield of cotton fibers.

2. Treatment with Plant Hormone

Plant hormones such as auxin, gibberellin, cytokinin and ethylene have been put to practical use widely for field crops or horticultural products. The influence of plant hormones on the fiber characteristics of cotton plants, particularly on the fiber elongation mechanism, is known by gibberellin, auxin or brassinolide; however, no effect has been fully confirmed yet, and it cannot be said that these plant hormones are effective for practical use.

3. Variety Improvement by Gene Recombination Technique

In recent years, gene recombinant technique has made remarkable progress, and several reports have been made on the successful variety improvement in certain kinds of plants (e.g., cotton, soybean, corn, tomato) by introduction and expression of a particular gene in these plants to confer a desired genetic trait thereon. There have been developed and put to practical use, for example, cotton plants with improved insect resistance by introduction of a gene coding for BT toxin (i.e., insecticidal protein toxin produced by *Bacillus thuringiensis*) or cotton plants with improved herbicide (Glyphosate) resistance by introduction of a gene coding for 5-enol-pyruvil-shikimic acid 3-phosphate synthetase.

If a gene associated with cotton fiber formation and elongation can be introduced into cotton plants and expressed in sufficient quantities, it would become possible to make a remarkable improvement in the characteristics or yield of cotton fibers. Further, the introduction of such a gene in anti-sense for makes it possible to suppress the action of this gene. In other words, it is believed that the characteristics and yield of cotton fibers can be controlled by introducing a gene associated with fiber formation and elongation into cotton plants, followed by large-scale expression or suppression of the gene. The method using such a genetic engineering technique can be expected to find wide applications, for example, more reliable control of fiber elongation and formation as compared with the conventional plant breeding by cross-breeding and screening. For this purpose, it is required that the mechanisms of fiber elongation and formation are elucidated on the genetic level and some genes closely associated with these mechanisms ark discovered and then actually expressed and regulated in the cotton fiber tissues to control the mechanisms of fiber elongation and formation.

At present, however, the knowledge of fiber elongation and formation in plants from the viewpoint of molecular biology is very limited. Although many studies have been made on the elongation of plant cells, most of the control factors remain unknown and the control mechanisms have not yet been elucidated.

A cotton fiber is composed of a single cell that has been differentiated from an epidermal cell of the seed coat, and it develops through four stages, i.e., initiation, elongation, secondary cell wall thickening and maturation stages. More specifically, the elongation of a cotton fiber begins with that of an epidermal cell of the ovule just after flowering and the cotton fiber rapidly elongates and then completes elongation in about 25 days after the flowering. After that, the fiber elongation is stopped, and a secondary cell wall is formed and grown through maturation to become a mature cotton fiber.

Some reports have been made on the isolation of such genes associated with the elongation and formation of cotton fibers. John et al. describe the isolation of E6 gene that is expressed preferentially in the cotton fiber tissues on the 15th and 24th days after flowering (see John, M. E. and Crow, L. J., *Proc. Natl. Acad. Sci. USA*, 89, 5769–5773 (1992)) or H6 gene coding for a proline-rich protein that actively functions in the formation of secondary cell walls (see John, M. E. and Keller, G., *Plant Physiol.*, 108, 669–676 (1995)). John further examined the effects of E6 gene on the cotton fiber characteristics by introduction of anti-sense E6 gene into cotton plants to reduce the expression level of endogenous E6 RNA (John, M. E., *Plant Molecular Biology*, 30, 297–306 (1996)). John, however, reported that although the expression level of E6 gene in fiber tissues is reduced, fiber length, fiber strength and fiber fineness are not significantly changed, and he concluded that E6 gene is not critical to the normal development of cotton fibers. Song et al. identified acyl carrier protein (ACP) cDNA from cotton plants by differential display method, which protein is specifically expressed in cotton fiber tissues (Song, P. and Allen, R. D., *Biochimika et Biophysica Acta*, 1351, 305–312 (1997)). As the gene associated with the cellulose synthesis in cotton fibers, cDNA coding for a catalytic subunit of cellulose synthase was isolated (Pear, J. R., Kawagoe, Y., et al., *Proc. Natl. Acad Sci. USA*, 93, 12637–12642 (1996)). Kasukabe, one of the present inventors, and his coworkers have isolated and identified five genes from cotton plants by differential screening method and differential display method, which genes are specifically expressed at the cotton fiber elongation stage (assignees' own U.S. Pat. No. 5,880,100 and U.S. patent applications Ser. Nos. 08/580,545, 08/867,484 and 09/262,653). Some genes associated with the elongation and formation of cotton fibers have already been isolated from cotton plants; however, none have succeeded in modifying the fiber characteristics of cotton plants in practice.

The analysis of molecular mechanisms of plant cell wall construction led to the isolation of endoxyloglucan transferase (EXGT) as an enzyme that catalyzes molecular grafting between polysaccharide cross-links in the plant cell wall matrix (Nishitani, K. and Tominaga, R., *J. Biol. Chem.*, 267, 21058–21064 (1992)). Xyloglucans are polysaccharides that cross-link individual cellulose microfibrils and play the main role in the net work structure of the cell wall involved in the cell elongation. For this reason, the transfer of xyloglucan cross-links by endoxyloglucan transferase is considered one of the important processes in the cell elongation. Some genes coding for endoxyloglucan transferase have been isolated from various plants including tomato (*Lycopersicon esculentum*) and mouse-ear cress (*Arabidopsis thaliana*) (Arrowsmith, D. A. and de Silva, J., *Plant Mol. Biol.*, 28, 391–403 (1995); Okazawa, K., Sato, Y., et al., *J. Biol. Chem.*, 268, 25364–25368 (1993)), and further from cotton plants (Gossypium spp.) (Shimizu, Y., Aotsuka, S., et al., *Plant Cell Physiol.*, 38(3), 375–378 (1997)). There is, however, no report that endoxyloglucan transferase genes isolated from various plants or from cotton plants are actually introduced into cotton plants and examined for the effects on the cotton fiber characteristics.

Most of the plant catalase species are localized on the microbodies and they are detoxification enzymes that decompose metabolically produced toxic $H_2O_2$ into water and oxygen. Their functions in plants have not yet been fully elucidated, although some reports have been made that catalase is associated with the low temperature tolerance and pathogen resistance of plants (Sanchez-Casas, P. and Klessing, D. F., *Plant Physiol.*, 106, 1675–1679 (1994); Prasad, T. K., Anderson, M. D., et al., *Plant Cell*, 6, 65–74 (1994)). There is, however, no report on the relationship between catalase and fiber characteristics of cotton plants.

Peroxidase is an enzyme that catalyzes the following oxidative reaction by hydrogen peroxide: $H_2O_2 + AH_2 \rightarrow 2H_2O + A$ Peroxidase genes have been isolated from various plants including tomato (*Lycopersicon esculentum*) and horseradish (*Armoracia rusticana*) (Roberts, E., Kolattukudy, P. E., *Mol. Gen. Genet.*, 217, 223–232 (1987); Fujiyama, K., Tekemura, H., et al., *Eur. J. Biochem.*, 173, 681–687 (1988)). Peroxidase is one of the cell wall enzymes and it exists through ionic bonding or covalent bonding in cell walls. One of the functions of peroxidase is the formation of lignin in the secondary components of cell walls. Peroxidase is considered to catalyze, in the presence of hydrogen peroxide, the reaction of forming dehydrogenation polymeric products from the lignin components (e.g., ferulic acid, p-coumaric acid) produced through shikimic acid pathway or cinnamic acid pathway (Gross, G. G. et al., *Planta*, 136, 271 (1977)). Another report describes that peroxidase is associated with the formation of intermolecular cross-links by the reaction of the respective tyrosine residues of two extensin molecules as the structural proteins of cell walls (Lamport, D. T. A., *MSU-DOE Plant Research Laboratory 7th Annual Report*, p. 65 (1982)). With respect to the relationship between peroxidase and cotton fibers, Rao et al. examined the peroxidase activity during the development of cotton fibers and showed that the peroxidase activity is lower in the cotton fiber elongation but significantly higher in the secondary wall thickening (Rao, N. R., Naithani, S. C., et al., *Z. Pflanzenphysiol. Bd.*, 106, 157–165 (1982)). These results suggest a possibility that peroxidase is involved in the rigidifying of cotton fiber cell walls. John et al. confirmed that fiber strength can be increased by introduction of a peroxidase gene into cotton plants and over-expression of the gene in the cotton fiber tissues (WO95/08914); however, they failed to obtain significant results on the fiber length or micronaire (i.e., fiber fineness).

As described above, some genes associated with the elongation and formation of cotton fibers have already been isolated; however, it seems to be the most important to actually introduce these genes into cotton plants to make sure of their effects on the level of practical use.

SUMMARY OF THE INVENTION

Under these circumstances, the present inventors have extensively studied the mechanisms of fiber elongation and formation in cotton plants from the viewpoints of molecular biology to improve the characteristics of cotton fibers. As a result, they have found that this purpose can be attained by introducing a gene coding for endoxyloglucan transferase, which is deeply associated with the cell elongation and greatly expressed in the cotton fibers and ovule tissues at the cotton fiber elongation stage, or a gene coding for catalase or peroxidase, which is a hydrogen peroxide eliminating enzyme, into cotton plants and over-expressing these genes in the cotton fiber cells, thereby completing the present invention.

Thus, the present invention provides a cotton plant of the genus Gossypium with improved cotton fiber characteristics, comprising an expression cassette containing a gene coding for an enzyme selected from the group consisting of endoxyloglucan transferase, catalase and peroxidase so that the gene is expressed in cotton fiber cells to improve the cotton fiber characteristics; and cotton fibers and cotton seeds obtained from the cotton plant.

The present invention further provides a method for producing cotton fibers with improved fiber characteristics, and cotton fibers obtained by this method. The method includes the steps of: transforming into a cotton plant of the genus Gossypium, an expression cassette containing a gene coding for an enzyme selected from the group consisting of endoxyloglucan transferase, catalase and peroxidase so that the gene is expressed in cotton fiber cells to improve the cotton fiber characteristics; growing the cotton plant transformant to form cotton bolls; and collecting cotton fibers from the cotton bolls of the plant.

BRIEF DESCRIPTION OF THE DRAWINGS

FIG. 3 is a diagram of the construction of plasmid pBI35S-prxC1a.

DETAILED DESCRIPTION OF THE INVENTION

Figure 1:
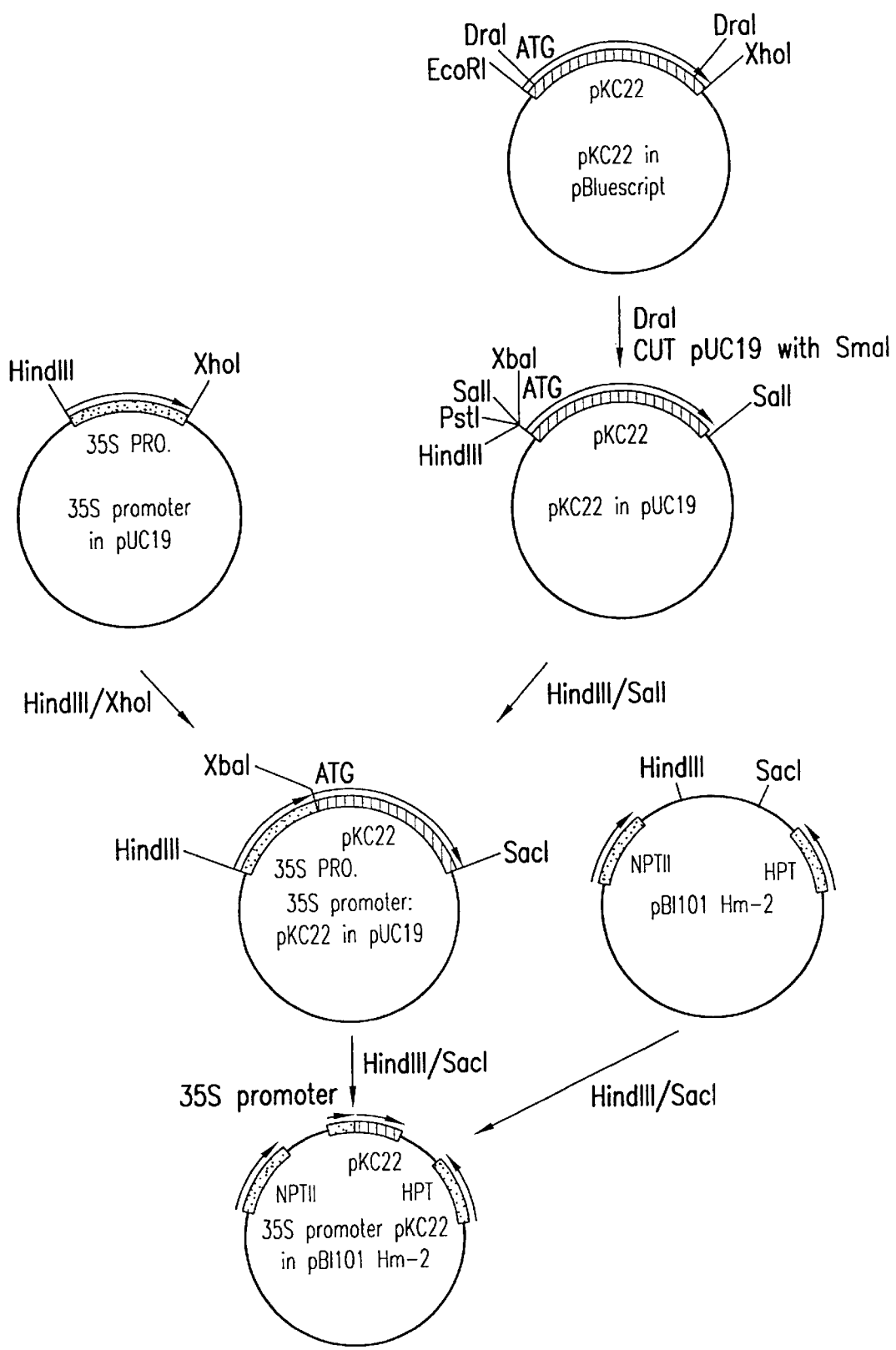
FIG. 1 is a diagram of the construction of plasmid pBI35S-22.

The present inventors have prepared cotton plant transformants that can exhibit the controlled expression of endoxyloglucan transferase, catalase or peroxidase gene by actually introducing each of these genes, together with an expression regulatory promoter, into cotton plants. They have evaluated the characteristics of cotton fibers obtained from these transformants and found that the fiber length, fiber strength and fiber fineness of these cotton fibers were significantly increased.

The term "endoxyloglucan transferase gene" as used herein refers to a gene coding for the amino acid sequence of an enzyme that catalyzes molecular grafting between polysaccharide cross-links in the plant cell wall matrix.

The term "catalase gene" as used herein refers to a gene coding for the amino acid sequence of an enzyme that catalyzes the decomposition of hydrogen peroxide, $H_2O_2 + H_2O_2 \rightarrow O_2 + 2H_2O$.

The term "peroxidase gene" as used herein refers to a gene coding for the amino acid sequence of an enzyme that catalyzes the reaction, $H_2O_2 + AH_2 \rightarrow 2H_2O + A$.

The term "expression cassette" as used herein refers to a DNA fragment comprising a gene sequence coding for the amino acid sequence of an enzyme such as endoxyloglucan transferase, catalase or peroxidase, which is operably linked to various regulatory elements that regulate the expression of the gene sequence, such as promoter sequences and enhancer sequences.

The term "cotton plant(s) that produces cotton fibers with improved fiber characteristics" as used herein refers to a cotton plant(s) that produces excellent cotton fibers as compared with the conventional cotton fibers with respect to fiber characteristics such as fiber length, fiber strength and fiber fineness; for example, Coker 312 (*Gossypium hirsutum*) as a typical variety of cotton plant can be rendered ability to produce cotton fibers with increased fiber length, fiber fineness and/or fiber strength.

The term "cotton plant(s)" as used herein refers to those of the genus Gossypium, examples of which are *Gossypium hirsutum, Gossypium barbadense, Gossypium arboreum, Gossypium anomalum, Gossypium armourianum, Gossypium klotzchianum, Gossypium herbaceum* and *Gossypium raimondii*.

The phrase "gene hybridizes to . . . under stringent conditions" means that the gene may be modified DNA which can be obtained by selecting DNA that hybridizes to DNA having the whole or part of the nucleotide sequence of SEQ ID NO: 1, 2 or 3 under stringent conditions. More particularly, the endoxyloglucan transferase gene may hybridize to a gene that has a nucleotide sequence extending from bps 32 to 901 of SEQ ID NO: 1, the catalase gene may hybridize to a gene that has a nucleotide sequence extending from bps 57 to 1541 of SEQ ID NO: 2, and the peroxidase gene may hybridize to a gene that has a nucleotide sequence extending from bps 1 to 1062 of SEQ ID NO: 3.

The term "stringent conditions" as used herein refers to those which make it possible that specific hybrids are formed but non-specific hybrids are not formed. The stringent conditions, although it is difficult to define them by numerical values, are exemplified by the case where modified DNA hybridizes to DNA having the whole or part of the nucleotide sequence of SEQ ID NO: 1, 2 or 3 under the hybridization conditions, i.e., at 42° C. with a salt concentration of 6×SSC (0.9 M NaCl, 0.09 M trisodium citrate) or 6×SSPE (3M NaCl, 0.2 M $NaH_2PO_4$, 20 mM EDTA.2Na, pH 7.4) and then the hybrid remains undissociated even under the washing conditions, i.e., at 42° C. with a salt concentration of 0.5×SSC.

The following will describe with typical examples the isolation of desired genes (i.e., endoxyloglucan transferase, catalase and peroxidase genes), the preparation of cotton plant transformants, and the evaluation of the characteristics of cotton fibers obtained from the transformants.

1. Isolation of Cotton Endoxyloglucan Transferase Gene (1) Construction of cDNA Library From the cotton ovules on the 5th day after the flowering, poly(A)$^+$ RNA is extracted by the ordinary method. Using the isolated poly(A)$^+$ RNA as a template, cDNA is synthesized using oligo(dT) primers and reverse transcriptase, and then converted into double-stranded DNA by the polymerase reaction. The double-stranded DNA is inserted into an appropriate vector, which is then used for the transformation of *Escherichia coli* (hereinafter referred to as *E. coli*) or other host cells to prepare a cDNA library.

The poly(A)$^+$ RNA isolation and cDNA synthesis may also be carried out using a commercially available cDNA cloning kit. Many kinds of vectors which can be used for library preparation are commercially available, such as λZAPII, λgt10 and λgt11. The host cell which can be used for transformation may include *E. coli* XL-1 Blue, *E. coli* XL-1 Blue MRF' and *E. coli* SURE.

(2) Screening of Desired Genes by Differential Screening Method

The phage plaque pattern of the cDNA library prepared by the above method in section 1(1) is replicated onto two filters, which are hybridized with each of the $^{32}$P-labelled cDNA probes prepared by the same method as described in section 1(1) from the ovules on the 5th day after the flowering and from the ovules on the 25th day after the flowering. The cDNA corresponding to the desired gene can be selected by detection of a positive hybridization signal only from the cDNA probe prepared from the ovules on the 5th day after the flowering.

The techniques necessary for the ordinary gene recombination such as RNA isolation, cDNA preparation, DNA digestion, ligation, transformation and hybridization are described in the instructional manuals of commercially available enzymes or agents used for the respective procedures or various text books (e.g., *Molecular Cloning* edited by Maniatis et al., Cold Spring Harbor, 1989, and *Current Protocols in Molecular Biology* edited by F. M. Ausubel et al., John Wiley & Sons, Inc., 1987).

The nucleotide sequence of the cloned cDNA can be determined by the Maxam-Gilbert method or the dideoxy chain termination method, each of which can be carried out using a commercially available kit. The nucleotide sequence may also be automatically determined with an autosequencer.

If the cDNA clone thus analyzed does not correspond to a full-length gene, a desired cDNA clone having such a full-length gene can be obtained by another plaque hybridization according to the ordinary method, or by the RACE (rapid amplification of cDNA ends) technique.

2. Isolation of Pea Catalase Gene (1) Construction of cDNA Library

From the leaves of pea seedlings on the 10th day after the germination, poly(A)$^+$ RNA is extracted by the ordinary method. Using the isolated poly(A)$^+$ RNA as a template, cDNA is synthesized using oligo(dT) primers and reverse transcriptase, and then converted into double-stranded DNA by the polymerase reaction. The double-stranded DNA is inserted into an appropriate vector, which is then used for the transformation of E. coli or other host cells to prepare a cDNA library.

The poly(A)+ RNA isolation and cDNA synthesis may also be carried out using a commercially available cDNA cloning kit. Many kinds of vectors which can be used for library preparation are commercially available, such as λZAPII, λgt10 and λgt11. The host cell which can be used for transformation may include E. coli XL-1 Blue, E. coli XL-1 Blue MRF$^v$ and E. coli SURE.

(2) Screening of Desired Genes by Plaque Hybridization Method

The phage plaque pattern of the cDNA library prepared by the above method in section 2(1) is replicated onto a filter, which is hybridized with a $^{32}$P-labelled cDNA probe corresponding to the cotton catalase gene (Ni W., Turley R. B. Trelease R. N., *Biochem. Biophys. Acta.*, 1049, 219–222 (1990)). The cDNA corresponding to the desired gene can be selected by detection of a positive hybridization signal.

The techniques necessary for the ordinary gene recombination such as RNA isolation, cDNA preparation, DNA digestion, ligation, transformation and hybridization are described in the instructional manuals of commercially available enzymes or agents used for the respective procedures or various text books (e.g., *Molecular Cloning* edited by Maniatis et al., Cold Spring Harbor, 1989, and *Current Protocols in Molecular Biology* edited by F. M. Ausubel et al, John Wiley & Sons, Inc., 1987).

The nucleotide sequence of the cloned cDNA can be determined by the Maxam-Gilbert method or the dideoxy chain termination method, each of which can be carried out using a commercially available kit. The nucleotide sequence may also be automatically determined with an auto-sequencer.

If the cDNA thus analyzed does not correspond to a full-length gene, a desired cDNA clone having such a full-length gene can be obtained by another plaque hybridization according to the ordinary method, or by the RACE (rapid amplification of cDNA ends) technique.

3. Isolation of Horseradish Peroxidase Gene (1) Construction of cDNA Library

From the cultured cells of horseradish, poly(A)+ RNA is extracted by the ordinary method. Using the isolated poly (A)+ RNA as a template, cDNA is synthesized using oligo (dT) primers and reverse transcriptase, and then converted into double-stranded DNA by the polymerase reaction. The double-stranded DNA is inserted into an appropriate vector, which is then used for the transformation of E. coli or other host cells to prepare a cDNA library.

The poly(A)+ RNA isolation and cDNA synthesis may also be carried out using a commercially available cDNA cloning kit. Many kinds of vectors which can be used for library preparation are commercially available, such as λZAPII, λgt10 and λgt11. The host cell which can be used for transformation may include E. coli XL-1 Blue, E. coli XL-1 Blue MRF$^v$ and E. coli SURE.

(2) Screening of Desired Genes by Colony Hybridization Method

The colony pattern of the cDNA library prepared by the above method in section 3(1) is replicated onto a filter, which is hybridized with a $^{32}$P-labelled cDNA probe that can be synthesized by a commercially available DNA synthesizer from the amino acid sequence of horseradish peroxidase (Welinder, K. G., *FEBS Lett.*, 72, 19–23 (1976)). The cDNA corresponding to the desired gene can be selected by detection of a positive hybridization signal.

The techniques necessary for the ordinary gene recombination such as RNA isolation, cDNA preparation, DNA digestion, ligation, transformation and hybridization are described in the instructional manuals of commercially available enzymes or agents used for the respective procedures or various text books (e.g., *Molecular Cloning* edited by Maniatis et al., Cold Spring Harbor, 1989, and *Current Protocols in Molecular Biology* edited by F. M. Ausubel et al, John Wiley & Sons, Inc., 1987).

The nucleotide sequence of the cloned cDNA can be determined by the Maxam-Gilbert method or the dideoxy chain termination method, each of which can be carried out using a commercially available kit. The nucleotide sequence may also be automatically determined with an auto-sequencer.

If the cDNA clone thus analyzed does not correspond to a full-length gene, a desired cDNA clone having such a full-length gene can be obtained by another plaque hybridization according to the ordinary method, or by the RACE (rapid amplification of cDNA ends) technique.

4. Preparation of Cotton Plant Transformants

Any of the genes obtained by the above method may be ligated to an appropriate promoter, followed by introduction into cotton plants, making it possible to increase the content of a desired enzyme such as endoxyloglucan transferase, catalase or peroxidase. In contrast, at least one part of the anti-sense strand (i.e., complementary sequence to the coding sequence) of the above gene may be ligated in reverse direction to an appropriate promoter, followed by introduction into cotton plants and then expression of the so-called anti-sense RNA, making it possible to decrease the content of a desired enzyme.

The method for transformation of cotton plants may include electro-poration in which plasmids are introduced by treatment of protoplasts with electric pulses; fusion of small cells, cells or lysosomes with protoplasts; microinjection; polyethylene glycol technique; and particle gun technique.

With the use of a plant virus as a vector, a desired gene can also be introduced into a cotton plant. A typical example of the plant virus which can be used is cauliflower mosaic virus (CaMV). The introduction of a desired gene is carried out, for example, as follows. First, a virus genome is inserted in a vector derived from E. coli or the like to prepare a recombinant, and a desired gene is inserted in the virus genome. The virus genome thus modified is removed from the recombinant by restriction endonuclease and inoculated into a cotton plant to insert the desired gene into the cotton plant (Hohn et al., *Molecular Biology of Plant Tumors*, Academic Press, New York, 549–560 (1982), and U.S. Pat. No. 4,407,956].

Further, there is a technique using a Ti plasmid of Agrobacterium. When a plant is infected with bacteria of the genus Agrobacterium, a part of their plasmid DNA is transferred to the plant genome. By making use of such a property, a desired gene can also be introduced into a cotton plant. Upon inoculation; for example, *Agrobacterium tumefaciens* and *Agrobacterium rhizogenes* induce the formation of crown galls and the formation of hairy roots, respectively. Each of these bacteria has a plasmid designated "Ti-plasmid" or "Ri-plasmid" having T-DNA (transferred DNA) and vir region. The tumor formation is caused by introduction of T-DNA into the genome of a plant, and then transcription and translation of an oncogene present in the T-DNA in the plant cells. The vir region per se is not transferred to the plant cells, but it is essential to the transfer of T-DNA. The vir region can also function even if it is on another plasmid different from the T-DNA containing plasmid (Nature, 303, 179 (1983)).

If a desired DNA is inserted in the T-DNA on the Ti- or Ri-plasmid, the desired DNA can be introduced into the plant genome upon inoculation of the plant with these bacteria of the genus Agrobacterium. In this case, a portion inducing the formation of crown galls or hairy roots is removed from the T-DNA of the Ti- or Ri-plasmid without deteriorating the desired transfer function, and the plasmid thus obtained can be used as a vector.

In the present invention, various other vectors can also be used, for example, vectors such as pBI121 (Clontech), which are designated "binary vectors". A desired gene is ligated in sense or anti-sense direction to an appropriate promoter, which is then inserted in the binary vector, followed by introduction into a plant. These binary vectors have no vir region, and the bacteria of the genus Agrobacterium to be used for introduction of these vectors are, therefore, required to contain another plasmid having vir region.

These vectors serve as a shuttle vector which can be amplified in E. coli as well as in the bacteria of the genus Agrobacterium. Accordingly, the recombination of Ti-plasmids can also be carried out with E. coli. These vectors have antibiotic-resistance genes, and the screening of transformants can, therefore, be readily done in the transformation of E. coli, bacteria of the genus Agrobacterium, or plants. These vectors further have CaMV 35S promoter, and the gene inserted in these vectors can, therefore, be introduced into the plant genome and then expressed under constitutive control.

The introduction of a desired gene by Agrobacterium in cotton plant cells and the regeneration of whole cotton plants from the transformed cells can be achieved, for example, as follows:

According to the ordinary method, seeds of a cotton plant are sowed on Stewart's seed germination media (Stewart's concentrate (detailed below), 0.75 g/l $MgCl_2$, 2.0 g/l Phytagel (Sigma), pH 6.8) and aseptically cultivated. The cotton seedlings are removed and hypocotyls are cut into small pieces. The desired gene is ligated to an appropriate promoter and subcloned in a plasmid having kanamycin resistance gene. This clone is transformed into Agrobacterium and its culture is diluted with MSNH (MS basal salts (Sigma), 30 g/l glucose, pH 5.8). The diluted Agrobacterium culture is used for the inoculation of the above hypocotyl pieces. The inoculated hypocotyl pieces are blotted on sterile filter paper to remove excess Agrobacterium solution, and placed on $T_2$ plates (MS basal salts (Sigma), 0.75 g/l $MgCl_2$, 0.1 mg/l 2,4-D, 0.5 mg/l Kinetin, 30 g/l glucose, 2.0 g/l Phytagel (Sigma), pH 5.8), followed by incubation for 3 days. The hypocotyl pieces are transferred to MS2NK KCL plats (MS basal salts (Sigma), 0.75 g/l $MgCl_2$, 30 g/l glucose, 2 mg/l NAA, 0.1 mg/l kinetin, 2.0 g/l Phytagel (Sigma), 50 mg/l kanamycin, 500 mg/l cefotaxime, pH 5.8) and incubated for 3 to 4 weeks to grow calluses. When the calluses are approximately 4 mm in size, they were removed from the hypocotyl and placed on fresh MS2NK KCL plates for further growth. When the calluses are sufficiently grown to approximately 1 cm in size, they are placed in MSNH liquid media containing kanamycin for embryo generation to begin the formation of suspension culture. The suspension culture is incubated until the cells become light green in color with some slightly round cells visible in the culture. The suspension culture containing fully grown cells is diluted with MSNH, which is applied to MSK 50K plates (MS basal salts (Sigma), 0.75 g/l $MgCl_2$, 1.9 g/l $KNO_3$, 30 g/l glucose, 2.0 g/l Phytagel (Sigma), 50 mg/l kanamycin, pH 5.8) and spread over the media surface, followed by incubation for somatic embryo development. The incubation is continued until embryos reached at least 1 mm in size, they are placed on SA plates (Stewart's concentrate (detailed below), 20 g/l sucrose, 20 g/l agar, pH 6.8) as embryo germination media. After continued incubation for some weeks, the roots are trimmed when they are observed, and the embryos are transferred to SGA plates (Stewart's concentrate (detailed below), 5 g/l sucrose, 0.75 g/l $MgCl_2$, 5.0 g/l agar, 1.5 g/l Phytagel (Sigma), pH 6.8), followed by incubation which is further continued until true leaves emerge. After emergence of the first true leaves, the cotton young plantlets can be moved to pint sized canning jars containing SGA media. When these cotton young plantlets reached approximately 10 cm in height and have several true leaves, they can be set in appropriate pots and cultivated in a green house. Cotton seeds and cotton fibers can be obtained from the cotton plant transformants thus regenerated.

From the transformants, DNA is extracted by the ordinary method and digested with appropriate endonuclease. Southern hybridization using the desired gene, which is the same as introduced into the transformants, as a probe makes it possible to determine whether transformation has occurred in the cotton plant.

In addition, from the transformants or non-transformants, RNA is extracted by the ordinary method, and a probe is prepared which has a sense or anti-sense sequence of the desired gene, which is the same as introduced into the transformants. Northern hybridization using these probes makes it possible to examine the degree of expression for the desired gene.

5. Evaluation of Cotton Fiber Characterizations

From the regenerated transformants, those which have the desired gene introduced therein and which express the desired gene are selected by Southern hybridization or Northern hybridization. The transformants thus selected are cultivated, from which T1 seeds are obtained and then examined whether they are homozygotes or heterzygotes to select cell lines having the desired gene surely introduced therein.

The cotton seeds of cell lines thus selected can be used for cultivation test in a closed greenhouse or in a separated field. The cultivation test is carried out as follows. The selected cotton seeds are sown by the ordinary method, and the cotton plants are grown to come into flower, followed by self-pollination. The subsequent opening of cotton bolls gives seed cotton, which is collected and subjected to machine ginning by the ordinary method to give cotton fibers, which can be examined for cotton fiber characteristics, for example, using the sorter method, the pressley method, the stereometer method or the HVI (high volume inspection machine) system method.

The present invention can attain the improvement of characteristics (e.g., fiber length, fiber fineness, fiber strength) of cotton fibers. With the use of cotton plants of the present invention, a novel variety of cotton plant having a genetically fixed trait of producing cotton fibers with improved fiber characteristics in high yield.

The present invention will be further illustrated by the following Examples; however, the present invention is not limited to these Examples.

EXAMPLE 1

Cloning of Cotton Plant Endoxyloglucan Transferase Gene

1. Preparation of Poly(A)+ RNA

The cotton plant, Supima (*Gossypium barbadense*), cultivated in a field was used as the test material. The ovules on the 5th day after the flowering and those on the 25th day after the flowering as a control sample were collected. About 5 g of each of the ovules thus obtained was immediately frozen in liquid nitrogen and pulverized with a mortar in the presence of liquid nitrogen. To the pulverized ovules was added 10 ml of 0.2 M Tris-acetate buffer for extraction (5 M guanidine thiocyanate, 0.7% β-mercaptoethanol, 1% polyvinylpyrrolidone (M.W., 360,000), 0.62% N-lauroylsarcosine sodium salt, pH 8.5), and the mixture was further pulverized with a polytron homogenizer (KINEMATICA) under ice cooling for 2 minutes. At that time, β-mercaptoethanol and polyvinylpyrrolidone were added to the buffer just before use. The pulverized mixture was then centrifuged at 17,000×g for 20 minutes, and the supernatant was collected.

The supernatant was filtered through a miracloth, and the filtrate was gently overlaid on 1.5 ml of 5.7 M cesium chloride in a centrifuge tube, followed by centrifugation at 155,000×g for 20 hours at 20° C. The supernatant was discarded, and the precipitated RNA was then collected. The precipitate was dissolved in 3 ml of TE buffer (10 mM Tris-HCl, 1 mM EDTA.2Na, pH 8.0), to which a mixture of phenol, chloroform and isoamyl alcohol (volume ratio, 25:24:1) was added at the same volume. The mixture was well agitated and then centrifuged at 17,000×g for 20 minutes, and the upper aqueous layer was collected. To the aqueous layer obtained were added a 0.1-fold volume of 3 M sodium acetate (adjusted to pH 6.2 by addition of gracious acetic acid) and a 2.5-fold volume of ethanol. The mixture was well agitated and allowed to stand without disturbance at −20° C. overnight. The mixture was then centrifuged at 17,000×g for 20 minutes, and the precipitate was washed with 70% ethanol and dried in vacuo.

The dry sample was dissolved in 500 µl of TE buffer to give a solution of the whole RNA. This RNA solution was incubated at 65° C. for 5 minutes and then immediately cooled on ice, to which 2×coupling buffer (10 mM Tris-HCl, 5 mM EDTA.2Na, 1M NaCl, 0.5% SDS, pH 7.5) was added at the same volume. The mixture was overlaid on an oligo-dT cellulose column (Clontech) which had been previously equilibrated with equilibration buffer (10 mM Tris-HCl, 5 mM EDTA.2Na, 0.5 M NaCl, 0.5% SDS, pH 7.5). The column was then washed with an about 10-fold volume of the same equilibration buffer as above, and the poly(A)+ RNA was eluted with elution buffer (10 mM Tris-HCl, 5 mM EDTA.2Na, pH 7.5).

To the eluate obtained were added a 0.1-fold volume of the same 3M sodium acetate as above and a 2.5-fold volume of ethanol, and the mixture was allowed to stand without disturbance at −70° C. The mixture was then centrifuged at 10,000×g, and the precipitate was washed with 70% ethanol and dried in vacuo. This dry sample was dissolved again in 500 µl of TE buffer, and purification with an oligo-dT cellulose column was repeated as described above. The poly(A)+ RNA obtained from the ovules on the 5th day after the flowering was used for the preparation of a cDNA library and a cDNA probe for differential screening, and the poly (A)+ RNA obtained from the ovules on the 25th day after the flowering was used for the preparation of a cDNA probe for differential screening.

2. Preparation of cDNA Library at Fiber Elongation Stage

The preparation of a cDNA library was carried out with ZAP-cDNA Synthesis Kit (Stratagene). The poly(A)+ RNA obtained from the ovules on the 5th day after the flowering in section 1 was used as a template, and double-stranded cDNA was synthesized using oligo(dT) primers and reverse transcriptase according to the method of Gubler and Hoffman et al. (*Gene*, 25, 263–269 (1983)).

To both ends of the cDNA obtained were ligated EcoR I adaptors (having Xho I and Spe I sites in the inside), and the ligated DNA was digested with Xho I. The fragment was then ligated between the EcoR I and Xho I sites of λ phage vector, λZAPII arm, and the vector was packaged with an in vitro packaging kit (Stratagene, GIGAPACK Gold), followed by injection into *E. coli* strain SURE (OD660=0.5), which afforded many recombinant λ phages serving as the cDNA library specific to the fiber elongation stage. This cDNA library had a size of $5.0 \times 10^6$.

3. Preparation of Probes

The poly(A)+ RNA prepared from the ovules on the 5th or 25th day after the flowering was used as a template, and cDNA was synthesized using oligo(dT) primers and reverse transcriptase M-MLV (Toyobo). After the synthesis, alkali hydrolysis treatment was carried out to remove the poly(A)+ RNA. The cDNA thus obtained was used as a template, and a $^{32}$P-labelled probe was prepared with Random Primed DNA Labeling Kit (USB).

The $^{32}$P-labelled probes thus prepared by the cDNA on the 5th day after the flowering and by the cDNA on the 25th day after the flowering were used as a probe for the fiber elongation stage and as a probe for the fiber non-elongation stage, respectively, for differential screening.

4. Screening of Genes Associated with Fiber Formation and Elongation

The above λ phages constituting the cDNA library from the ovules at the, fiber elongation stage were injected into *E. coli*, which was then grown on LB agar medium. About 50,000 plaques of λ phage DNA were replicated on two nylon membranes (Hybond-N, Amersham).

The nylon membranes having replicated λ phage DNA were placed on a filter paper containing a solution for alkali denaturation (0.5 M NaOH, 1.5 M NaCl) and allowed to stand for 4 minutes. The nylon membranes were placed on a filter paper containing a solution for neutralization (0.5 M Tris-HCl, 1.5 M NaCl, pH 8.0) and allowed to stand for 5 minutes. After washing with 2×SSC (0.3 M NaCl, 0.03 M trisodium citrate), these membranes were subjected to DNA fixation with Stratalinker (Stratagene). The nylon membranes thus treated for DNA fixation were prehybridized in hybridization buffer (50% formamide, 0.5% SDS, 6×SSPE (3M NaCl, 0.2 M $NaH_2PO_4$, 20 mM EDTA-2Na, pH 7.4), 5×Denhardt solution (0.1% Ficoll, 0.1% polyvinylpyrrolidone, 0.1% bovine serum albumin), 50 mg/l denatured salmon sperm DNA) at 42° C. for 3 hours, and the cDNA probes prepared in section 3 were added to the respective membranes, followed by hybridization at 42° C. for 20 hours. The membranes were then removed and washed with solutions each containing 2×SSC, 1×SSC, 0.5×SSC or 0.1×SSC at 42° C. for 1 to 2 hours. These membranes were dried and then allowed to adhere closely to X-ray films for exposure overnight.

As a result, 34 positive clones hybridized with the probe for the fiber elongation stage rather than for the fiber non-elongation stage were selected. The particularly strongly hybridized clone was designated KC22 and further analyzed.

From the phage DNA of KC22, plasmid clone pKC22 having a cDNA insert was prepared with ZAP-cDNA Synthesis Kit (Stratagene) by the in vivo excision method.

First, 200 μl of KC22-containing phage solution, 200 μl of E. coli XL1-Blue suspension and 1 μl of helper phage R408 suspension was mixed and then incubated at 37° C. for 15 minutes, followed by the addition of 3 ml of 2×YT medium. A shaken culture was grown at 37° C. for 2 hours and then treated at 70° C. for 20 minutes, followed by centrifugation at 4000×g for 10 minutes, and the supernatant was collected. Then, 30 μl of the supernatant was mixed with 30 μl of E. coli SURE suspension, and the mixture was incubated at 37° C. for 15 minutes and then inoculated on several microliters of LB agar medium containing 50 ppm ampicillin, followed by incubation at 37° C. overnight. The colony-forming E. coli contained the plasmid clone pKC22 having the cDNA insert.

The nucleotide sequence of the cDNA insert in the plasmid was determined by the dideoxy chain termination method (Messing, *Methods in Enzymol.*, 101, 20–78 (1983)). The resulting nucleotide sequence is shown in the Sequence Listing, SEQ ID NO: 1.

The search for the homology between the nucleic acid sequences of this gene and various known genes in the data base revealed that KC22 has homology to the endoxyloglucan transferase genes isolated from other plants such as red bean and tomato (Nishitani et al, *J. Biol. Chem.*, 268, 25364–25368 (1993)) and to the meri-5 gene which is specifically expressed in an apical meristem of Arabidopsis (Medford, J. I., Elmer, J. S., and Klee, H. J., *Plant Cell*, 3, 359–370 (1991)).

EXAMPLE 2

Isolation of Pea Catalase Gene

The isolation of genes from a pea plant (*Pisum sativum*) was carried out by the method as described in *Plant Molecular Biology*, 17, 1263–1265 (1991). The isolated pea catalase gene was designated CAT. The nucleotide sequence of the gene is shown in Sequence Listing, SEQ ID NO: 2.

EXAMPLE 3

Isolation of Horseradish Peroxidase Gene

The isolation of genes from horseradish (*Armoracia rusticana*) was carried out by the method as described in *Eur. J. Biochem.*, 173, 681–687 (1988). The isolated horseradish peroxidase gene was designated prxC1a. The nucleotide sequence of the gene is shown in Sequence Listing, SEQ ID NO: 3.

EXAMPLE 4

Preparation of Cotton Plant Transformants
1. Construction of Plasmids

A plasmid with an expression cassette containing an endoxyloglucan transferase gene and a 35S promoter was prepared by the scheme as shown in FIG. 1. The nucleotide sequence of SEQ ID NO: 1 (KC22) was digested with Dra I so as to contain the open reading frame. The Dra I fragment was subcloned into the Sma I site of plasmid pUC19. This plasmid was digested with Sma I and Hin dIII, in which a Hin dIII/Xho I fragment of a 35S promoter was subcloned. This clone was digested with Hin dIII and Sac I, and the fragment was subcloned between the Hin dIII and Sac I sites of binary vector pBI101-Hm2 having kanamycin resistance gene (NPTII) and hygromycin resistance gene (HPT). This plasmid was designated pBI35S-22 and transformed into E. coli JM109. The resulting E. coli JM109 transformant was designated E. coli JM109/pBI35S-22.

Figure 2:
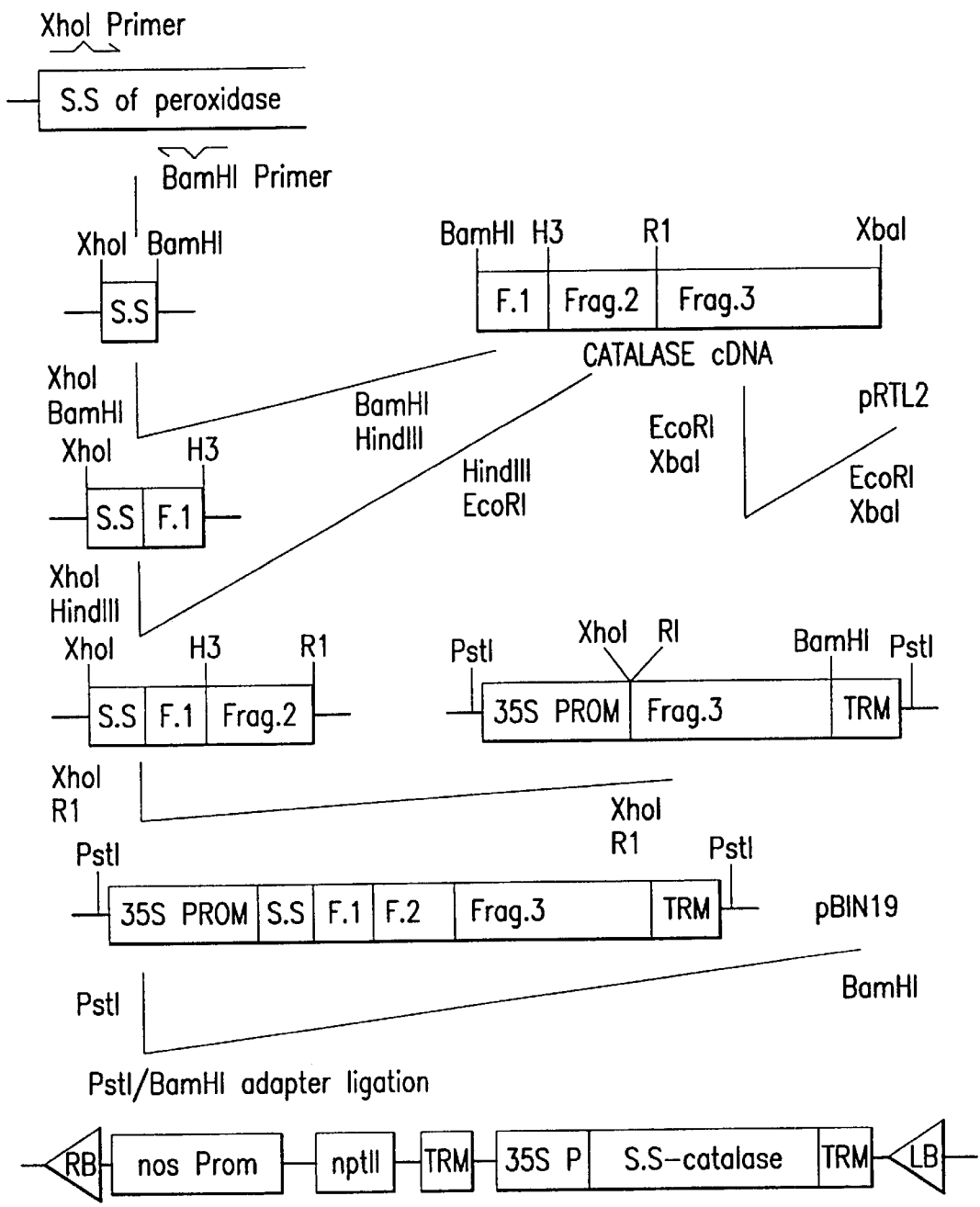
FIG. 2 is a diagram of the construction of plasmid pBIN35S-S.S-CAT.

The plasmid with an expression cassette containing a catalase gene, a signal sequence and a 35S promoter was prepared by the scheme as shown in FIG. 2. In the expression cassette, the signal sequence (S.S.) corresponding to a signal peptide associated with the passage of an extracellular protein through the cell membrane was inserted between the 35S promoter and the catalase gene. The signal sequence was amplified from the cotton plant cDNA library by PCR using primers with Xho I and Bam HI restriction sites, respectively, according to the ordinary method, and subcloned in vector pRTL2. On the other hand, the nucleotide sequence of SEQ ID NO: 2 (CAT) was separated into the following three fragments: fragment 1 by digestion with Bam HI and Hin dIII; fragment 2 by digestion with Hin dIII and Eco RI; and fragment 3 by digestion with Eco RI and Xba I. Fragments 1 and 2 were ligated to the signal sequence, while fragment 3 was inserted between the 35S promoter (35S PROM) and the terminator sequence (TRM). The fragment containing the signal sequence ligated to fragments 1 and 2 was digested with Xho I and Eco RI, and the fragment was subcloned between the 35S promoter and the fragment 3. This clone was digested with Pst I, and the fragment was subcloned in binary vector pBIN19 having kanamycin resistance gene (nptII) with a Bam HI adapter. This plasmid was designated pBIN35S-S.S-CAT and transformed into E. coli JM109. The resulting E. coli transformant was designated E. coli JM109/pBIN35S-S.S-CAT.

Figure 3:
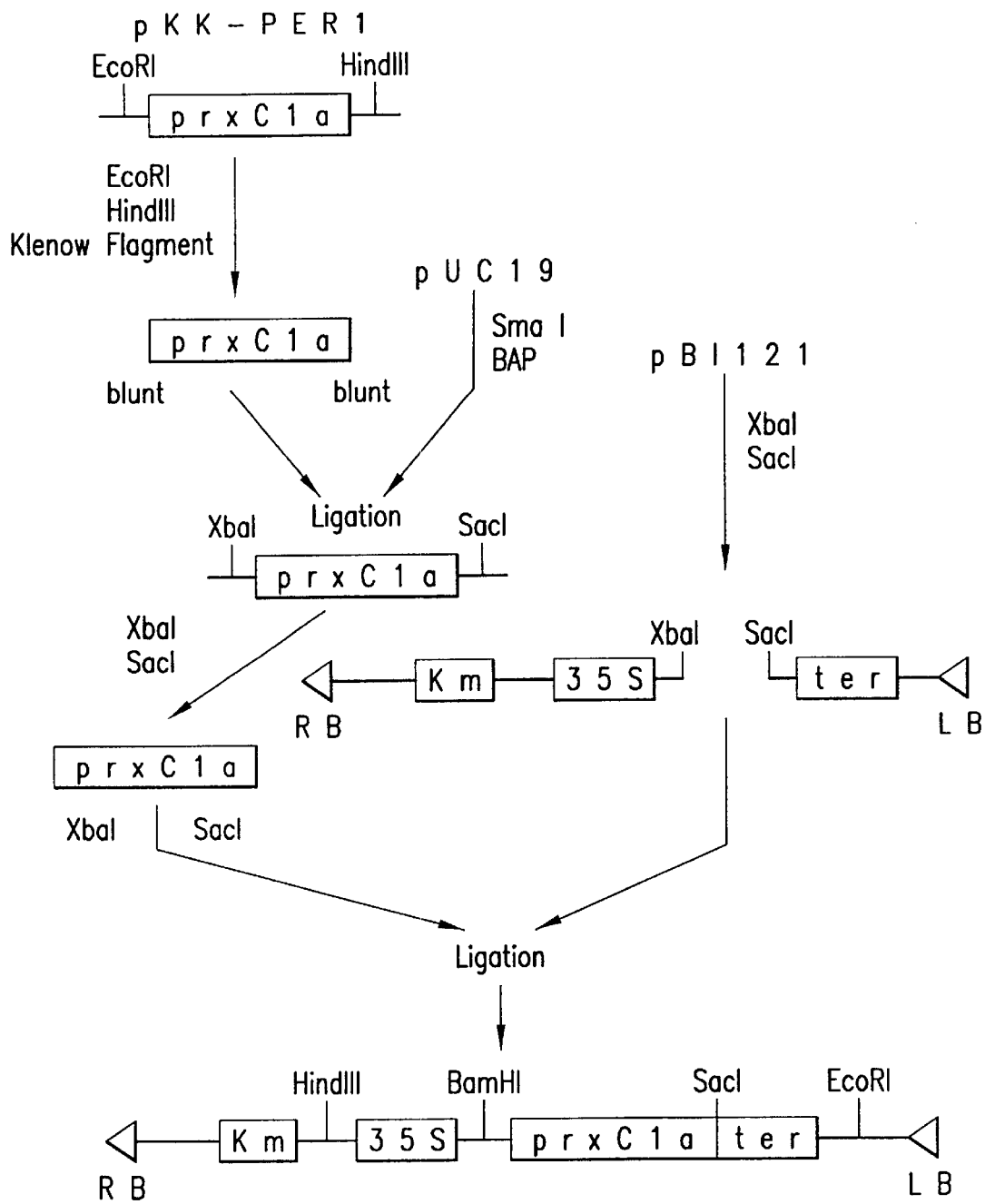

The plasmid with an expression cassette containing a peroxidase gene and a 35S promoter was prepared by the scheme as shown in FIG. 3. Plasmid vector pKK-PER1 was digested with Eco RI and Hin dIII so as to contain the open reading frame in the nucleotide sequence of SEQ ID NO: 3 (prxC1a). This fragment was blunt-ended with a Klenow fragment and subcloned into the Sma I site of plasmid pUC19. This plasmid was digested with Xba I and Sac I, and the fragment was subcloned between the Xba I and Sac I sites of binary vector pBI121 having kanamycin resistance gene (Km) and a 35S promoter. This plasmid was designated pBI35S-prxC1 and transformed into E. coli JM109. The resulting E. coli transformant was designated E. coli JM109/pBI35S-prxC1a.

2. Introduction of Each Plasmid into Agrobacterium

The transformant E. coli JM109/pBI35S-22, JM109/pBIN35S-S.S-CAT or JM109/pBI35S-prxC1a obtained in section 1 and E. coli strain HB101 containing helper plasmid pRK2013 were separately cultured on LB media containing 50 mg/l of kanamycin at 37° C. overnight, while the Agrobacterium strain EHA101 was cultured on LB medium containing 50 mg/l of kanamycin at 37° C. over two successive nights. The bacterial cells were harvested by taking 1.5 ml of each culture in an Eppendorf tube, and then washed with LB medium. These bacterial cells were suspended in 1 ml of LB medium, after which three kinds of bacteria were mixed together in 100 μl portions. The mixture was plated on LB agar medium and incubated at 28° C. to ensure the conjugation transfer of plasmids to Agrobacterium. After 1 to 2 days, a part of the medium was scratched with a sterile loop and spread over LB agar medium containing 50 mg/l kanamycin. The incubation was continued at 28° C. for 2 days, and a single colony was selected. The resulting transformants were designated EHA101/pBI35S-22, EHA101/pBIN35S-S.S-CAT and EHA101/pBI35S-prxC1a.

3. Preparation of Test Plants
(1) Seed Sterilization and Germination
Cotton seeds were soaked in 70% ethanol with stirring for 30 seconds. The seeds were then collected in a sieve and rinsed with 100 ml of sterilized water. The seeds were then soaked in Clorox/Tween 20 solution and shaken at 110 rpm for 20 minutes. The seeds were collected in a sieve and rinsed with 100 ml of sterilized water. The seeds were soaked in sterilized water with shaking for 2 minutes and collected in a sieve. The rinsing steps were repeated twice, and the seeds were finally soaked in sterilized water for 30 to 60 minutes. The seeds were collected in a sieve and placed on germination media (100 ml Stewart's concentrate/liter, pH 6.8 with 1 M KOH, 2.0 g/l Phytagel (Sigma)) in 25×150 mm culture tubes and incubated at 30° C. for 7 to 10 days.

(2) Hypocotyl Inoculation

Two milliliter cultures of the Agrobacterium containing the gene constructs were grown in the presence of appropriate antibiotics at 30° C. for 24 hours. The cultures were diluted in the ratio of 19:1 with MSNH (MS basal salts (Sigma), 30 g/l glucose, pH 5.8) in a sterile Petri dish. Cotton seedlings (7 to 10 days after sowing) were removed from the culture tubes and placed on a sterile aluminum foil cutting pad. Cotyledons and roots were excised and discarded, and the hypocotyls were cut into pieces of 6 to 8 mm in length. The hypocotyls were placed in the diluted Agrobacterium cultures and incubated for at least 30 seconds. The hypocotyl pieces were removed and blotted on sterile filter paper to remove excess Agrobacterium solution. The hypocotyl pieces were placed on Petri dishes containing $T_2$ media (MS basal salts (Sigma), 0.75 g/l $MgCl_2$, 0.1 mg/l 2,4-D, 0.5 mg/l kinetin, 30 g/l glucose, 2.0 g/l Phytagel (Sigma), pH 5.8) at a ratio of 8 to 10 hypocotyl pieces per dish. Approximately 200 to 300 hypocotyl pieces (20 to 30 plates) were used for each inoculation. The dishes that contained the inoculation hypocotyls were incubated in the dark at room temperature for 3 days. The hypocotyls were removed from the $T_2$ plates, blotted on sterile filter paper, and transferred to MS2NK KCL plates (MS basal salts (Sigma), 0.75 g/l $MgCl_2$, 30 g/l glucose, 2 mg/l NAA, 0.1 mg/l kinetin, 2.0 g/l Phytagel (Sigma), 1 ml of 50 mg/ml kanamycin/liter, 5 ml of 100 mg/ml cefotaxime/liter, pH 5.8; 45 to 50 ml of media per Petri dish). These plates were sealed with Parafilm to prevent drying. These plates incubated under the light at 30° C.

(3) Callus Growth

The hypocotyls incubated on MS2NK KCL plates were transferred once per month or as needed to avoid contamination and overgrowth of the Agrobacterium. The transformed callus began to appear in 3 to 4 weeks. The transformed callus was light green or white in color, and appeared to be smooth and dense rather than loose and fluffy.

When the calluses were approximately 4 mm in size, they were removed from the hypocotyl and placed on separate MS2NK KCL plates to encourage faster growth. When the individual calluses are approximately 1 cm in size, they were transferred into suspension culture to begin generation of embryos. The time required to reach this stage of growth was typically 3 to 5 months.

(4) Embryo Generation

The calluses were placed in a 50 ml of Erlenmeyer flask containing 10 ml of MSNH and 5 μl of 50 mg/ml kanamycin. The calluses were broken into small pieces using a sterile spatula. Suspension cultures were incubated on a shaker at 110 rpm in a lighted area at 30° C. The cultures were ready to plate in 2 to 8 weeks when the cells became light green in color with some small, white slightly round cells visible in the cultures.

(5) Plating Suspension Cultures

The suspension cultures were poured into sterile 50 ml tubes and the cells were allowed to settle to the bottom of the tubes. The MSNH was removed and 20 to 30 ml of fresh MSNH was added to rinse the cells. The tubes were shaken and the cells were allowed to settle to the bottom again. This rinsing procedure was repeated twice.

After the cells settled to the bottom of the tubes, the cell volume was estimated and the MSNH used to rinse the cells was removed and the cells resuspended in MSNH so that they were diluted at a ratio of 0.5 ml of cells in 9.5 ml of MSNH. Two milliliter aliquots of this suspension was applied to MSK 50K plates (MS basal salts (Sigma), 0.75 g/l $MgCl_2$, 1.9 g/l $KNO_3$, 30 g/l glucose, 2.0 g/l Phytagel (Sigma), 1 ml of 50 mg/ml kanamycin/liter, pH 5.8), and spread evenly over the media surface. The plates were incubated under the light at 30° C. until the surface of the plates were dry and then sealed with Parafilm.

(6) Embryo Selection

All of the plates were examined at least one each month for somatic embryo development. The somatic embryos became visible on some of the plates after about 3 weeks. When the embryos reached at least 1 mm in size, they were placed on SA plates (100 ml Stewart's concentrate/liter, 20 g/l sucrose, 20 g/l agar, pH 6.8; pour about 20 ml in each Petri dish) to begin the germination process. The other potentially embryogenic cells were removed to fresh MSK 50K plates. These cells were usually light green rather than brown or white, and were round and glassy looking. If a particular cell line did not produce any embryogenic cells, some of the green non-embryogenic cells were washed with MSNH and replated as described above.

(7) Embryo Germination

After the embryos were selected from the MSK 50K plates, they were placed on SA plates and then incubated without Parafilm sealing to begin desiccation. The plates were incubated in the dark at 30° C. for approximately 2 weeks. After two weeks, the roots were trimmed and the embryos were transferred to SGA plates (Stewart's concentrate, 5 g/l sucrose, 0.75 g/l $MgCl_2$, 1.5 g/l Phytagel (Sigma), 5 g/l agar, pH 6.8; pour about 30 ml in each Petri dish). The SGA plates were incubated in the light at 30° C. without Parafilm sealing. The embryos were transferred to new SGA plates as the old plates dried out, and the roots were trimmed each time they were transferred. The germinated embryos remained on the SGA plates until true leaves emerged.

(8) Cotton Plants

After the first true leaves emerged, the young plantlets were moved to pint sized canning jars containing SGA media (same as SGA plates, except that approximately 60 ml of media should be added to each jar). When the plants reached 7 to 10 cm in height and had several true leaves, the top was cut off and transferred to another jar. The cuttings had 3 to 4 leaves. The parent plants were maintained in jars in case the cuttings accidentally died in the greenhouse.

When the cuttings developed a good root system, but before the roots turned black, they were transplanted into one gallon pots containing potting soil. The plants were hardened by placing large Zip-lock bags over the plants and the top of the pot. After two weeks, the corners of the bag were cut off and left for one week. The top was then cut completely open and left or one more week. The bags were then removed, and the hardened plants ere moved to the greenhouse.

The Stewart's concentrate (10×) used herein was prepared from the following materials:

| Macronutrients | |
|---|---|
| KNO$_3$ | 20.24 g |
| NH$_4$NO$_3$ | 9.60 g |
| MgSO$_4$.7H$_2$O | 19.72 g |
| CaCl$_2$.2H$_2$O | 7.04 g |
| KH$_2$PO$_4$ | 1.08 g |
| Micronutrients | |
| Fe EDTA | 220 mg |
| Boric acid | 74 mg |
| MnSO$_4$.4H$_2$O | 202.8 mg |
| ZnSO$_4$.7H$_2$O | 103.6 mg |
| KI | 10 mg |
| NaMoO$_2$. 2H$_2$O | 8.8 mg |
| CuSO$_4$.5H$_2$O | 0.3 mg |
| CoCl$_2$.6H$_2$O | 0.284 mg |
| Vitamins | |
| Nicotinic acid | 19.6 mg |
| Pyridoxine HCl | 32.8 mg |
| Thiamine HCl | 54 mg |

This will make 4 liters of concentrate, which is enough for 40 liters of media. This concentrate was frozen in aliquots of 100 ml.

EXAMPLE 5

Field Test of Transformants

1. Selection of Cell Lines Having Desired Genes Introduced Therein

The transformants as prepared in Example 4 were subjected to the cultivation test in a closed greenhouse attached to Texas Tech University. The introduction of a desired gene was checked by Northern analysis and the cotton fibers were evaluated for fiber characteristics. Cell lines having the desired genes surely introduced and expressed were selected. The selected cell lines are shown in Table 1.

TABLE 1

| Introduced gene | Cell line |
|---|---|
| KC22 | 7-114#5-34 |
| KC22 | 114#41-3 |
| KC22 | 114#46-10 |
| CAT | R-9#15-1 |
| CAT | 9-52-16 |
| prxC1a | 11#27-31-1 |
| prxC1a | 11#14-12C |
| prxC1a | 11#14-12A |

2. Cultivation Test in Separated Field

The seeds of the cell lines shown in Table 1 and a control cotton plant (Coker 312) were used as the test samples. These seeds were sown in a separated field. These cotton plants began flowering, at which time they underwent self-pollination. In a few subsequent months, young healthy leaves were collected from all the transformants under cultivation, and examined for the expression of the desired genes introduced therein by Northern analysis using these genes as probes according to the ordinary method. After opening, cotton bolls were collected and dried. Seed cotton was collected and subjected to machine ginning in the Texas A&M Agricultural Experiment Station to separate cotton fibers from the seeds. The cotton fibers were evaluated for fiber characteristics such as (1) fiber length by the sorter method and fiber strength by the pressley method; and (2) fiber length, fiber strength and fiber fineness by 900 HVI system (Spinlab). The results are shown in Tables 2 and 3 for fiber characteristics (1) and (2), respectively.

TABLE 2

| Introduced gene | Cell line | Fiber length (inch) | Fiber strength (1000 Lbs/in$^2$) |
|---|---|---|---|
| non-transformant | Coker 312 | 1.21 ± 0.03 | 86.4 ± 2.6 |
| KC22 | 7-114#5-34 | 1.31 ± 0.03 | 91.0 ± 3.2 |
| KC22 | 114#41-3 | 1.35 ± 0.02 | 87.9 ± 3.3 |
| KC22 | 114#46-10 | 1.32 ± 0.03 | 90.5 ± 2.4 |
| CAT | R-9#15-1 | 1.20 ± 0.03 | 95.0 ± 4.4 |
| CAT | 9-52-16 | 1.30 ± 0.03 | 95.3 ± 5.1 |
| prxC1a | 11#27-31-1 | 1.26 ± 0.04 | 90.9 ± 4.1 |
| prxC1a | 11#14-12C | 1.28 ± 0.04 | 88.7 ± 3.2 |
| prxC1a | 11#14-12A | 1.31 ± 0.02 | 88.6 ± 1.5 |

TABLE 3

| Introduced gene | Cell line | Fiber length (inch) | Fiber strength (g/tex) | Fiber fineness (µg/inch) |
|---|---|---|---|---|
| non-transformant | Coker 312 | 1.15 ± 0.04 | 24.2 ± 1.7 | 4.00 ± 0.54 |
| KC22 | 7-114#5-34 | 1.29 ± 0.02 | 26.9 ± 1.0 | 4.80 ± 0.10 |
| KC22 | 114#41-3 | 1.24 ± 0.01 | 27.5 ± 0.4 | 4.90 ± 0.10 |
| KC22 | 114#46-10 | 1.28 ± 0.02 | 28.0 ± 0.8 | 4.65 ± 0.07 |
| CAT | R-9#15-1 | 1.15 ± 0.03 | 28.9 ± 1.2 | 5.05 ± 0.21 |
| CAT | 9-52-16 | 1.25 ± 0.02 | 28.2 ± 0.6 | 4.80 ± 0.30 |
| prxC1a | 11#27-31-1 | 1.25 ± 0.01 | 28.2 ± 1.2 | 4.10 ± 0.10 |
| prxC1a | 11#14-12C | 1.26 ± 0.02 | 26.1 ± 1.2 | 4.33 ± 0.26 |
| prxC1a | 11#14-12A | 1.28 ± 0.02 | 25.6 ± 1.5 | 4.15 ± 0.07 |

As can be seen from Tables 2 and 3, all the cell lines (i.e., 7-114#5-34, 114#41-3 and 114#46-10) of the transformants having cotton plant endoxyloglucan transferase gene (KC22) introduced therein exhibited a remarkable increase both in fiber length and in fiber fineness. In addition, all the cell lines (i.e., R-9#15-1 and 9-52-16) of the transformants having pea catalase gene (CAT) introduced therein exhibited a remarkable increase both in fiber strength and in fiber fineness, whereas all the cell lines (i.e., 11#27-31-1, 11#14-12C and 11#14-12A) of the transformants having horseradish peroxidase gene (prxC1a) introduced therein exhibits a remarkable increase in fiber length.

These findings show that the introduction of a gene coding for such a specific enzyme in cotton plants can attain a significant improvement of fiber characteristics, e.g., fiber length and fiber fineness in the case of cotton plant endoxyloglucan transferase gene (KC22); fiber strength and fiber fineness in the case of pea catalase gene (CAT); and fiber length in the case of horseradish peroxidase gene (prxC1a).

What is claimed is:

1. A cotton plant of the genus Gossypium with improved cotton fiber characteristics, comprising an expression cassette containing a polynucleotide coding for peroxidase operably linked to a promoter that directs expression in cotton fiber cells, so that the polynucleotide is expressed in cotton fiber cells to improve fiber length, fiber fineness, or fiber strength as compared to a non-transformed cotton plant.

2. The cotton plant according to claim 1, wherein the polynucleotide coding for peroxidase is derived from a plant.

3. The cotton plant according to claim 1, wherein the polynucleotide coding for peroxidase has a nucleotide sequence extending from bps 1 to 1062 of SEQ ID NO:3.

4. The cotton plant according to claim 1, which is selected from the group consisting of *Gossypium hirsutum*, *Gossypium barbadense*, *Gossypium arboreum*, *Gossypium anomalum*, *Gossypium armourianum*, *Gossypium klotzchianum*, *Gossypium herbaceum* and *Gossypium raimondii*.

5. Cotton fibers obtained from the cotton plant according to claim 1.

6. Cotton seeds obtained from the cotton plant according to claim 1, wherein the cotton seeds comprise the expression cassette of claim 1.

7. A method for producing cotton fibers with improved fiber characteristics, which comprises the steps of:

transforming into a cotton plant of the genus Gossypium, an expression cassette containing a polynucleotide coding for peroxidase operably linked to a promoter that directs expression in cotton fiber cells, so that the gene is expressed in cotton fiber cells to improve fiber length, fiber fineness, or fiber strength as compared to cotton fiber cells from a non-transformed cotton plant;

growing the cotton plant transformation to form cotton bolls; and collecting cotton fibers from the cotton bolls of the plant.

8. The method according to claim 7, wherein the polynucleotide coding for peroxidase is derived from a plant.

9. The method according to claim 8, wherein the polynucleotide coding for peroxidase is derived from a plant.

10. The method according claim 7, wherein the polynucleotide coding for peroxidase has a nucleotide sequence extending from bps 1 to 1062 of SEQ ID NO: 3.

11. The method according to claim 7, wherein the cotton plant of the genus Gossypium is selected from the group consisting of *Gossypium hirsutum*, *Gossypium barbadense*, *Gossypium arboreum*, *Gossypium anomalum*, *Gossypium armourianum*, *Gossypium klotzchianum*, *Gossypium herbaceum* and *Gossypium raimondii*.

12. Cotton fibers obtained from the method according to claim 7.

* * * * *

UNITED STATES PATENT AND TRADEMARK OFFICE
CERTIFICATE OF CORRECTION

PATENT NO.    : 6,559,363 B1
DATED         : May 6, 2003
INVENTOR(S)   : Yoshihisa Kasukabe et al.

It is certified that error appears in the above-identified patent and that said Letters Patent is hereby corrected as shown below:

<u>Title page,</u>
Item [75] Inventor, please change the order of the Inventor's names to read as follows:
-- Yoshihisa Kasukabe
  Izumi Ihara
  Yoshihiko Maekawa
  Randy Dale Allen --

Signed and Sealed this

Twenty-third Day of September, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,559,363 B1
DATED         : May 6, 2003
INVENTOR(S)   : Yoshihisa Kasukabe et al.

It is certified that error appears in the above-identified patent and that said Letters Patent is hereby corrected as shown below:

<u>Title page,</u>
Item [73] Assignee, revise to read as follows:
-- [73] Assignee: Toyo Boseki Kabushiki Kaisha, Osaka-fu, Japan, and Texas Tech University, Lubbock, Texas. --

Signed and Sealed this

Twenty-fifth Day of May, 2004

JON W. DUDAS
*Acting Director of the United States Patent and Trademark Office*